United States Patent
Le Neel et al.

(10) Patent No.: US 9,448,198 B2
(45) Date of Patent: Sep. 20, 2016

(54) MICROSENSOR WITH INTEGRATED TEMPERATURE CONTROL

(75) Inventors: Olivier Le Neel, Singapore (SG); Suman Cherian, Singapore (SG); Ravi Shankar, Singapore (SG)

(73) Assignee: STMICROELECTRONICS PTE LTD., Singapore (SG)

( * ) Notice: Subject to any disclaimer, the term of this patent is extended or adjusted under 35 U.S.C. 154(b) by 491 days.

(21) Appl. No.: 13/176,599

(22) Filed: Jul. 5, 2011

(65) Prior Publication Data

US 2013/0010826 A1     Jan. 10, 2013

(51) Int. Cl.
| | |
|---|---|
| G01K 1/00 | (2006.01) |
| G01K 13/00 | (2006.01) |
| G01K 17/00 | (2006.01) |
| G01N 25/00 | (2006.01) |
| G01N 27/327 | (2006.01) |
| G01N 33/49 | (2006.01) |

(52) U.S. Cl.
CPC .......... *G01N 27/3272* (2013.01); *G01N 33/49* (2013.01)

(58) Field of Classification Search
USPC .................................... 374/163, 142, 31, 45
See application file for complete search history.

(56) References Cited

U.S. PATENT DOCUMENTS

| | | | | |
|---|---|---|---|---|
| 5,140,393 A * | 8/1992 | Hijikihigawa et al. | ....... | 257/252 |
| 5,545,300 A * | 8/1996 | Yun et al. | ...... | 204/424 |
| 5,683,569 A * | 11/1997 | Chung et al. | ........ | 205/775 |
| 5,700,360 A * | 12/1997 | Chan | ........ | G01N 27/404 204/403.06 |
| 6,093,308 A * | 7/2000 | Lewis et al. | ........ | 205/787 |
| 6,238,085 B1 * | 5/2001 | Higashi et al. | ........ | 374/10 |
| 6,294,133 B1 * | 9/2001 | Sawada | ........ | G01K 7/015 204/400 |
| 6,326,229 B1 * | 12/2001 | Mastromatteo et al. | ........ | 438/49 |
| 6,331,074 B1 * | 12/2001 | Kimura | ........ | 374/10 |
| 6,387,329 B1 * | 5/2002 | Lewis et al. | ........ | 422/98 |
| 6,436,346 B1 * | 8/2002 | Doktycz et al. | ........ | 422/51 |
| 6,551,838 B2 * | 4/2003 | Santini et al. | ........ | 436/174 |
| 6,902,701 B1 * | 6/2005 | Hughes et al. | ........ | 422/83 |

(Continued)

FOREIGN PATENT DOCUMENTS

| | | |
|---|---|---|
| CN | 1112239 A | 11/1995 |
| CN | 1485618 A | 3/2004 |

(Continued)

OTHER PUBLICATIONS

Zhu at al., "Planar Amperometric Glucose Sensor Based on Glucose Oxidase Immobilized by Chitosan Film on Prussian Blue Layer," Sensors 2:127-136, 2002.

*Primary Examiner* — Mirellys Jagan
(74) *Attorney, Agent, or Firm* — Seed IP Law Group PLLC

(57) ABSTRACT

Microsensors that include an integrated thermal energy source and an integrated temperature sensor are capable of providing localized heating and temperature control of individual sensing regions within the microsensor. Localized temperature control allows analyte detection to be carried out at the same temperatures or substantially the same temperatures at which the sensor is calibrated. By carrying out the sensing near the calibration temperature, more accurate results can be obtained. In addition, the temperature of the sensing region can be controlled so that chemical reactions involving the analyte in the sensing region occur near their peak reaction rate. Carrying out the sensing near the peak reaction rate improves the sensitivity of the sensor which is important as sensor dimensions decrease and the magnitude of the generated signals decreases.

17 Claims, 6 Drawing Sheets

(56) References Cited

U.S. PATENT DOCUMENTS

| | | | |
|---|---|---|---|
| 7,033,840 B1* | 4/2006 | Tagge et al. | 436/147 |
| 7,100,283 B1 | 9/2006 | Grdodian et al. | |
| 7,338,637 B2* | 3/2008 | Pease et al. | 422/68.1 |
| 7,692,219 B1* | 4/2010 | Holm-Kennedy | 257/253 |
| 7,694,346 B2* | 4/2010 | Adams | G01N 29/036 250/234 |
| 7,768,650 B2 | 8/2010 | Bazylenko | |
| 7,914,735 B2* | 3/2011 | Torres | G01K 17/006 422/50 |
| 8,323,982 B2* | 12/2012 | LeBoeuf et al. | 436/164 |
| 8,346,337 B2* | 1/2013 | Heller | A61B 5/14532 422/82.01 |
| 8,449,824 B2* | 5/2013 | Sun | 422/82.01 |
| 8,562,806 B2* | 10/2013 | Janata | G01N 33/5438 204/600 |
| 8,617,381 B2* | 12/2013 | Sun | A61B 5/01 204/400 |
| 8,647,577 B2* | 2/2014 | Hinz | G01N 27/4148 422/69 |
| 8,722,417 B2* | 5/2014 | Ahmad | A61B 5/097 422/400 |
| 2002/0142478 A1 | 10/2002 | Wado et al. | |
| 2003/0039586 A1* | 2/2003 | Toyoda et al. | 422/98 |
| 2004/0151629 A1* | 8/2004 | Pease et al. | 422/68.1 |
| 2005/0034307 A1 | 2/2005 | Brzezinski | |
| 2005/0076943 A1* | 4/2005 | Cooper et al. | 136/224 |
| 2005/0142034 A1* | 6/2005 | Kim et al. | 422/82.01 |
| 2005/0241959 A1* | 11/2005 | Ward | G01N 27/4146 205/792 |
| 2006/0154401 A1* | 7/2006 | Gardner et al. | 438/53 |
| 2006/0263255 A1* | 11/2006 | Han | B82Y 10/00 422/83 |
| 2007/0045756 A1* | 3/2007 | Chang et al. | 257/414 |
| 2008/0081769 A1* | 4/2008 | Hassibi | 506/9 |
| 2008/0110230 A1 | 5/2008 | Guay et al. | |
| 2008/0221806 A1* | 9/2008 | Bryant | G01N 27/127 702/22 |
| 2009/0098657 A1* | 4/2009 | Blais | A61B 5/14532 436/147 |
| 2009/0102925 A1 | 4/2009 | Sheard et al. | |
| 2009/0159445 A1* | 6/2009 | Krishna | G01N 27/4162 204/424 |
| 2010/0094111 A1* | 4/2010 | Heller et al. | 600/345 |
| 2010/0163410 A1 | 7/2010 | Mastromatteo et al. | |
| 2010/0186234 A1 | 7/2010 | Binder | |
| 2011/0209524 A1 | 9/2011 | Ziglioli et al. | |
| 2011/0228809 A1* | 9/2011 | Tadigadapa | 374/31 |
| 2011/0318840 A1 | 12/2011 | Ziglioli et al. | |
| 2012/0006102 A1* | 1/2012 | Bryant | G01N 27/127 73/61.43 |
| 2012/0076171 A1* | 3/2012 | Wu | G01K 1/20 374/183 |
| 2013/0040374 A1* | 2/2013 | Tachibana | B01L 3/5027 435/287.1 |
| 2013/0289477 A1* | 10/2013 | Wolpert et al. | 604/66 |
| 2014/0134607 A1* | 5/2014 | Lin | G01N 27/327 435/5 |
| 2014/0335630 A1* | 11/2014 | Cameron | G01N 33/5308 436/501 |
| 2015/0064693 A1* | 3/2015 | Khattak | G01N 33/54366 435/5 |
| 2015/0079583 A1* | 3/2015 | Baudenbacher | B01L 3/502784 435/5 |
| 2016/0077031 A1* | 3/2016 | Lechner | G01N 27/124 436/50 |

FOREIGN PATENT DOCUMENTS

| | | |
|---|---|---|
| CN | 1767898 A | 5/2006 |
| IT | TO2010 000067 A | 7/2011 |
| WO | 2005/006968 A1 | 1/2005 |
| WO | 2010/023610 A1 | 3/2010 |

* cited by examiner

MICROSENSOR WITH INTEGRATED TEMPERATURE CONTROL

BACKGROUND

1. Technical Field

The present application relates to an integrated semiconductor device including a sensor or sensors for sensing and identifying analytes in a sample under investigation.

2. Description of the Related Art

The demand for microsensors of small dimensions has led to the study of integrated solutions that use techniques and knowledge acquired in the manufacture of semiconductors. In particular, detection and diagnostic devices of a disposable type, which may be connected to external apparatuses for chemical and biochemical analyses, have been studied.

Detection and diagnostic devices, utilizing microsensors, comprise a solid substrate, generally of a flat type, bearing a chip, to which particular sensors are connected. These sensors may be sensitive to various analytes, including, for example biomolecules (DNA, RNA, proteins, antigens, antibodies, hormones, etc.), micro-organisms or parts thereof (bacteria, viruses, spores, cells, etc.), and chemicals (oxygen, carbon monoxide, carbon dioxide, glucose, etc.). These microsensors are generally of a type that have limited use, either in the number of times a particular microsensor is used, or in what the microsensor is designed to detect.

For example, a common limited use microsensor is used in a handheld blood glucose meter for diabetics. Checking a person's blood glucose level usually involves a painful prick of a finger to draw out a droplet of blood. The drawn blood is placed in contact with a testing strip, which has a transducer in the form of various electrodes that are sensitive to a chemical reaction between the glucose in the blood and glucose oxidase on one of the electrodes. Signals from the electrodes are detected and processed to determine a blood glucose number that is displayed on a screen to the user.

Miniaturization of microsensors translates into smaller sample volumes and requires smaller device dimensions. With the smaller sample volumes and smaller device dimensions, the electric signal produced by an electrochemical sensor can decrease to the order of nano- or pico amperes. With such small electric signals and the need for accurate and reproducible results, controlling the conditions at which the measurements are taken becomes increasingly important.

Conditions such as temperature are known to directly affect the rate of chemical reactions. For example, there is an optimum temperature above which the reaction rate between glucose and glucose oxidase does not increase. This temperature sensitivity results in an increasing current output from the transducer as the temperature approaches the optimum reaction temperature and a decreasing current response as the temperature increases beyond the optimum reaction temperature. By controlling the temperature of the microsensor in the local region where the chemical reaction occurs, the current output from the transducer can be maximized which will result in increased sensitivity and a reduction in the effect of interfering signals.

The temperature at which a microsensor is used can affect the accuracy of the sensor in other ways. For example, if the sensor is calibrated at a specific temperature and the testing is carried out at a different temperature, the accuracy of the measurement can be adversely affected.

In addition, in some bio- or chemical microsensors, the analyte is required to diffuse through a membrane to reach the transducer. The permeability of the membrane can depend on the identity of the diffusing species and the temperature. When the permeability of the membrane is affected by temperature, the accuracy of the measurement will decrease when the measurement is carried out at a temperature different from the calibration temperature.

BRIEF SUMMARY

Solutions to controlling the temperature at which analytes of interest are detected by a microsensor are described in the present disclosure. In certain embodiments, a semiconductor device including a microsensor capable of detecting a small amount of analyte in a sample is described. In such embodiments, the microsensor produces a signal, e.g., an electric or optical signal, in response to the concentration of analyte present in the sample. The disclosed microsensors include a sensing region formed over a semiconductor substrate. The sensing region includes a transducer that produces a signal in response to an interaction between the analyte and the sensing region. The microsensors include an integrated thermal energy source that produces thermal energy and an integrated temperature sensor that detects the temperature of the sensing region. The thermal energy source and temperature sensor are adjacent to the sensing region and cooperate to provide localized heating and temperature control of the sensing region.

By controlling the temperature of the sensing region to be at or near the temperature at which the sensor was calibrated, the accuracy of the measurements can be improved. In addition, the sensitivity of the microsensor can be increased by controlling the temperature of the sensing region to approach the temperature at which an interaction between the analyte and the sensing region is near its peak. For example, in embodiments where the transducer is an electrochemical transducer and the interaction is a chemical reaction, the temperature of the sensing region is controlled to a temperature where the chemical reaction rate is at its maximum.

In some embodiments, the thermal energy source is provided below the transducer. In some embodiments, the thermal energy source is also provided below the temperature sensor. In yet other embodiments, both the thermal energy source and the temperature sensor are provided below the transducer. In yet other embodiments, the thermal energy source and temperature sensor do not underlie the transducer. In certain embodiments, the transducer and temperature sensor are formed from the same material. In other embodiments, the transducer and the temperature sensor are formed from different materials.

The present disclosure describes that the thermal energy source generates thermal energy that provides localized heating of the sensing region. The integrated temperature sensor detects the temperature of the sensing region and produces a signal indicative of that temperature. That signal can be used by a control unit to control the thermal energy produced by the thermal energy source. Through this feedback loop, localized heating of the sensing region can be adjusted and controlled to achieve the desired temperature.

The microsensors described by the present disclosure can be formed as a semiconductor device through a sequence of growing, deposition, patterning, and etching steps. In one embodiment, such a method involves providing a silicon substrate that includes a thermal insulation layer. A thermal energy source layer of a refractory material is formed over the thermal insulation layer. The resulting thermal energy source layer is patterned to form a thermal energy source. A thermal conducting layer is formed over the thermal energy source. After the thermal conducting layer is formed, a working electrode, a counter electrode, and a temperature sensor are formed over the thermal conducting layer. A passivation layer is then formed over the temperature sensor. The passivation layer is patterned to define a sensing region and expose at least a portion of the working electrode and counter electrode.

DETAILED DESCRIPTION

Figure 1:
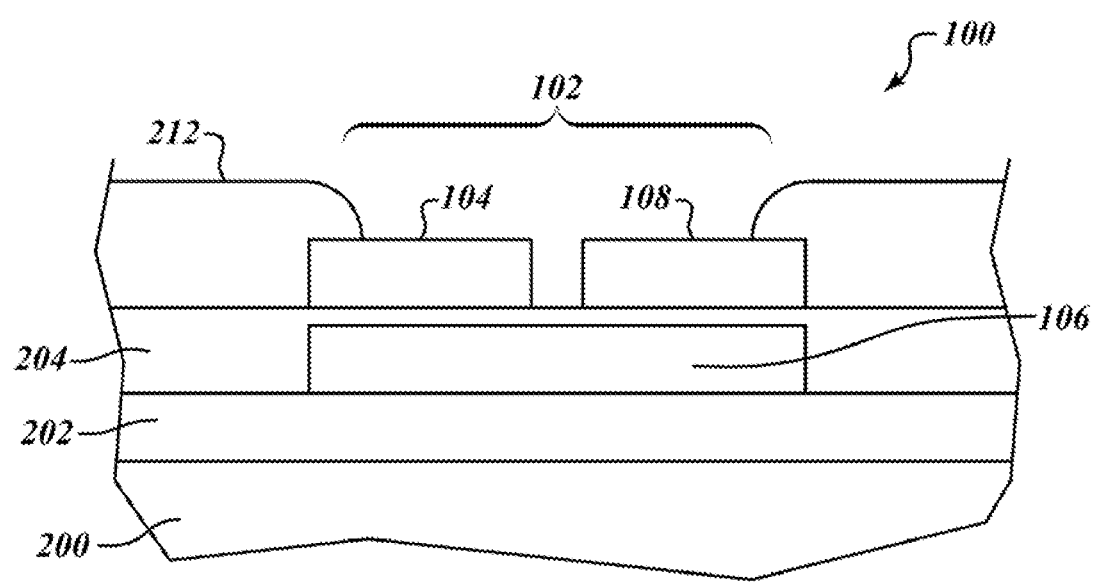
FIG. 1 is a schematic view of a cross-section for a microsensor according to one embodiment of the present disclosure.

In the following description, certain specific details are set forth in order to provide a thorough understanding of various aspects of the disclosed subject matter. However, the disclosed subject matter may be practiced without these specific details. In some instances, well-known structures and methods of forming the structures associated with semiconductor devices have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same aspect. Furthermore, the particular features, structures, or characteristics may be combined in any suitable manner in one or more aspects of the present disclosure.

Reference throughout the specification to "chemical or biological element" or "chemical" includes all chemical atoms, parts of atoms, molecules, particulates, biological material, etc. that are sensed and interact with the sensors described herein. The term "chemical" should not be construed narrowly to limit a chemical element solely to an atom or a molecule, but rather, the term "chemical" is broadly construed to cover chemical and biological elements or components thereof.

Throughout the following description a transducer is described in terms of an electrochemical transducer that includes a working electrode, a counter electrode and an optional reference electrode. It is noted that the reference to an electrochemical transducer and its electrodes is for illustrative purposes only and is not to be construed as limiting the scope of the described embodiments and appended claims. For example, the transducer may be an electrical transducer that measures surface or electrolyte conductivity. Other examples of transducers include optical (measures fluorescence, reflection, or adsorption) transducers, mass sensitive or heat sensitive transducers.

In the drawings, identical reference numbers identify similar features or elements. The sizes and relative positions of the features in the drawings are not necessarily drawn to scale.

FIG. 1 shows a microsensor 100 formed as part of a semiconductor device in accordance with the present disclosure. FIG. 1 is a schematic view that does not show elements such as metal interconnect lines, vias, contact pads, and other conventional features. These features can be provided using known structures and processing techniques. As an overview, in FIG. 1 sensor 100 includes a sensing region 102 into which a sample (not shown) containing an analyte of interest is received. Sensing region 102 includes a transducer 104 that produces a signal in response to an interaction between the analyte and the sensing region. The sensor also includes a temperature sensor 108, a thermal energy source 106, and an underlying thermal insulating layer 202 (e.g., silicon dioxide). Thermal insulating layer 202 is formed on an underlying semiconductor substrate 200, e.g., silicon substrate.

This underlying semiconductor substrate 200 may include various conductive and non-conductive features needed to operate the sensor. For example, semiconductor substrate 200 may include metal interconnect features, vias, contact pads and the like to provide electric power to thermal energy source 106 and process signals from transducer 104 and temperature sensor 108. These components can be provided using known structures and processing techniques and are not described in detail.

Thermal insulating layer 202 thermally insulates underlying semiconductor substrate 200 from thermal energy source 106. Layer 202 can be formed from silicon dioxide using conventional thermal growth or deposition processes. Other dielectric materials with a similar or lower coefficient of thermal conductivity can be used in place of silicon dioxide.

As shown in FIG. 1, a thermal energy source 106 is formed on thermal insulating layer 202 adjacent sensing region 102. The thermal energy source 106 is formed from a refractory material, such as co-sputtered tantalum aluminum, and generates thermal energy in response to the flow of electric current. Materials for forming thermal energy source 106 are not limited to tantalum aluminum. Other refractory materials such tantalum nitride can be used. A layer 204 that preferably has high thermal conductivity is between the thermal energy source 106 and the transducer 104.

Positioned above thermal energy source 106 and forming a part of sensing region 102 is a transducer 104. Though not shown in FIG. 1, transducer 104 includes a plurality of electrodes, for example, a working electrode, counter electrode, and an optional reference electrode formed from inert polarizable metals that are suitable for electrochemistry, including gold, platinum, palladium, and silver. While working electrode, counter electrode, and optional reference electrode are illustrated schematically as a single structure 104 in FIG. 1; it should be understood that transducer 104 comprises multiple electrodes. These electrodes cooperate to detect a change in electrical properties resulting from an interaction between an analyte of interest and the sensing region 102. For example, when microsensor 100 functions as an electrochemical sensor, the working electrode of transducer 104 may have a chemical receptor (not shown) formed on its surface. For example, the receptors may be biologic cells, antibodies, enzymes, DNA/RNA sequences or customized molecules that chemically react with the analyte of interest in a manner that can be detected by the electrodes. While the present disclosure describes embodiments that employ an electrochemical sensor, other responses to the interaction of the analyte with the sensing region, such as optical, capacitive, frequency, gravimetric and the like can also be used to detect the analyte of interest.

In the embodiment illustrated in FIG. 1, temperature sensor 108 is adjacent heater 106 and transducer 104. More specifically, in FIG. 1, sensor 108 is above heater 106. Like transducer 104, temperature sensor 108 is located within sensing region 102 where it can readily detect a temperature of sensing region 102. Like transducer 104, a portion of temperature sensor 108 is exposed and not covered by passivation layer 212. Temperature sensor 108 can be a thermistor made from a material that exhibits an electrical resistance that changes with temperature, such as platinum or chromium silicide. Temperature sensor 108 can be formed from suitable metals other than platinum or chromium silicide.

As shown in FIG. 1, portions of transducer 104 and temperature sensor 108 are covered by a passivation layer 212, formed from a material such as polyimide. Other portions of the transducer 104 and temperature sensor 108 are exposed and not covered by passivation layer 212. These uncovered portions of transducer 104 and temperature sensor 108 define a sensing region 102 where a sample containing the analyte of interest is received. Once received in the sensing region 102, the analyte interacts with the sensing region 102, for example, by undergoing a chemical reaction at the working electrode this chemical reaction is detected as an electric signal by the electrodes of the transducer.

While reference is made to a sensing region that relies upon electrochemical principles to detect an analyte, the present invention is not limited to sensing regions that rely on electrochemical principles. For example, the sensing region can rely on other types of interactions between the analyte and the sensing region such as those that produce other types of measurable signals such as optical signals, changes in mass, changes in acoustic properties, changes in thermal conductivity properties or changes in thermal diffusivity properties.

Figure 2:
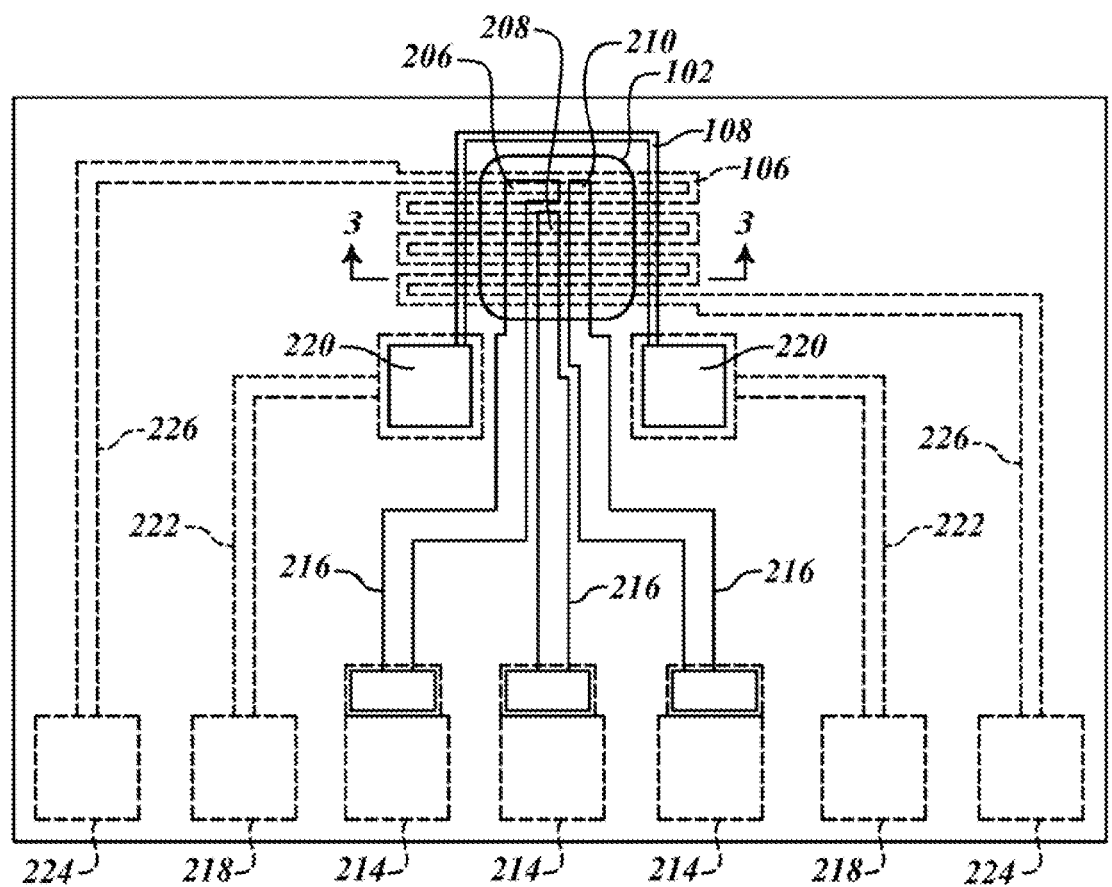
FIG. 2 shows a top plan view of a layout for a microsensor according to one embodiment.
Figure 3:
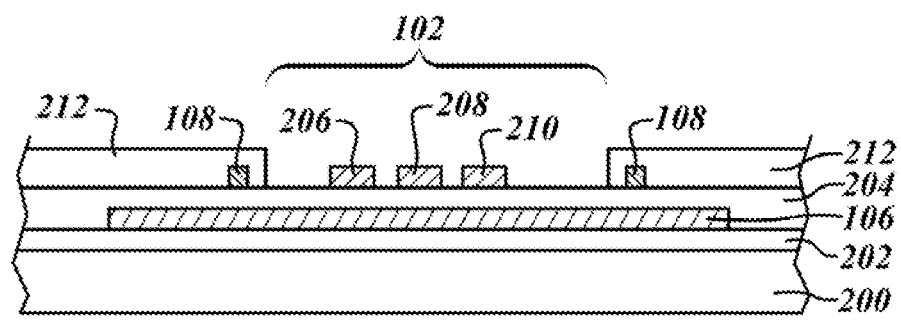
FIG. 3 shows a cross-section view taken along line 3-3 in FIG. 2.

Referring to FIGS. 2 and 3, FIG. 2 shows a top plan view of a microsensor including sensing region 102, metal features forming thermal energy source 106, electrodes 206, 208 and 210, and temperature sensor 108 according to a specific embodiment. In this embodiment, the transducer 104 is composed of electrodes 206, 208 and 210. FIG. 3 shows a cross-sectional view taken along line 3-3 in FIG. 2.

Sensing region 102 includes a counter electrode 206, a working electrode 208, and a reference electrode 210. Counter electrode 206, working electrode 208, and reference electrode 210 are electrically connected to contact pads 214 by conventional metal interconnect lines 216 formed as interlayer metallization components. Counter electrode 206, working electrode 208, and reference electrode 210 can be connected via contact pads 214 and lines 216 to other devices which might be part of the transducer 104 such as a potentiostat (not shown), and also to an analog-to-digital (ND) converter (not shown), and a microprocessor (not shown) for operating the electrodes, collecting signals, and processing the signals.

Temperature sensor 108 extends around three sides of the sensing region 102. Each end of temperature sensor 108 is connected to a contact pad 218 through a combination of an interlayer via 220 and interlayer metallization lines 222. Temperature sensor 108 may be connected to additional devices such as an analog/digital converter and a microprocessor to collect electric signals that are related to the temperature of sensing region 102. The microprocessor is preferably capable of receiving signals from the temperature sensor 108 and controlling the thermal output by thermal energy source 106 based on the signals received from temperature sensor 108. In this manner, controlled localized heating is provided to the sensing region 102.

As best illustrated in FIG. 3, temperature sensor 108 is covered by a passivation layer 212. In this embodiment, the temperature sensor 108 is covered by layer 212 at all locations and not exposed to the open environment as shown in FIG. 1. Portions of counter electrode 206, working electrode 208, and reference electrode 210 remain exposed through an opening in passivation layer 212. This opening defines a well for receiving a sample. When the temperature of sensing region 102 changes, the temperature as sensed by temperature sensor 108 will change, resulting in a change in the resistance of temperature sensor 108. This change in resistance can be detected and converted into a temperature reading using known components and techniques. Accordingly, temperature sensor 108 is able to sense the temperature of the sensing region 102. As described above, the temperature sensed by temperature sensor 108 can be utilized by a microprocessor to control the thermal output of thermal energy source 106.

In the embodiment of FIGS. 2 and 3, located below counter electrode 206, working electrode 208, reference electrode 210, and temperature sensor 108 is a thermal energy source 106. Thermal energy source 106 is separated from temperature sensor 108 and electrodes 206, 208, 210 by a thermal conducting layer 204. Thermal energy source 106 is a serpentine element with each end electrically connected to separate contact pads 224 by interconnect metallization lines 226. Thermal energy source 106 is separated from underlying silicon substrate 200 by thermal insulating layer 202 formed from a material having a thermal conductivity similar to silicon dioxide.

By providing the thermal energy source 106 directly adjacent to, e.g., below, the sensing region 102, localized heating can be provided to the sensing region. Localized heating has the advantage of not affecting the temperature of adjacent sensing regions where different interactions would be sensed. In addition, localized heating heats the regions of interest, i.e., sensing region, while minimizing heating of regions outside the sensing region that may contain components adversely affected if they were heated to the same temperatures as the sensing region.

In addition to the arrangement of thermal energy source 106 and temperature sensor 108 shown in FIGS. 1-3, other arrangements can provide localized heating as described below with reference to FIGS. 5-7.

Figure 4A:
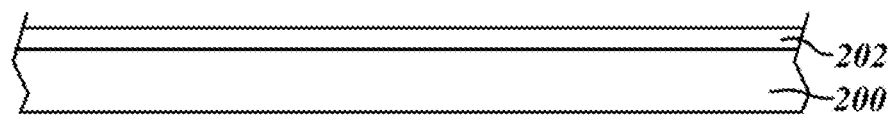
FIGS. 4A-4G show a cross-section view of different steps in the process flow for making a microsensor in accordance with one embodiment of FIG. 2.

FIGS. 4A-4G show one method for forming a semiconductor device that includes a microsensor in accordance with the present disclosure. As shown in FIG. 4A, the microsensor is formed on a silicon substrate 200 on which a thermal insulating layer 202 of silicon dioxide has been formed using known techniques such as thermal oxidation.

Figure 4B:
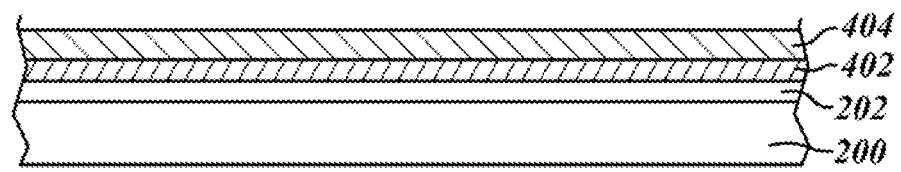
Figure 4C:
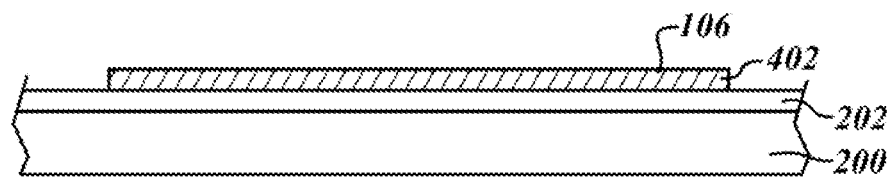
Figure 4D:
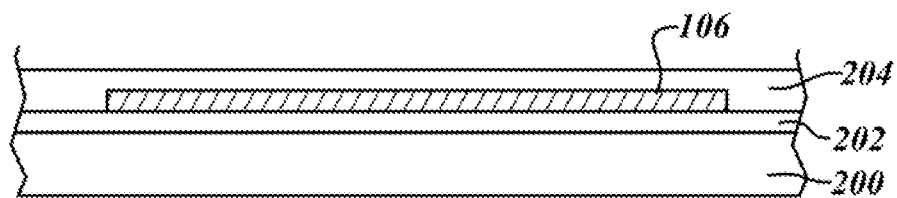
Figure 4E:
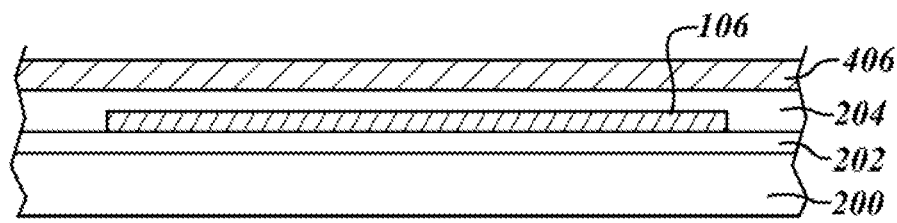

As shown in FIG. 4B, a layer 402 of a refractory material such as tantalum aluminum is deposited over thermal insulating layer 202. Tantalum aluminum can be deposited using known metal deposition techniques such as a sputtering or chemical vapor deposition. After the tantalum aluminum is deposited, a layer 404 of aluminum is deposited thereover. Aluminum layer 404 can be deposited using known metal deposition techniques, such as physical vapor deposition. Following the formation of tantalum aluminum layer 402 and aluminum layer 404, the aluminum layer 404 is patterned to form contacts and interconnect lines not shown in FIG. 4C but shown in FIG. 2 to form interconnect lines such as 216, 222, 226, etc. Tantalum aluminum layer 402 is then patterned to form thermal energy source 106. The formed thermal energy source 106 is then covered with a thermal conducting layer 204 as shown in FIG. 4D. Thermal conducting layer 204 is formed from materials that have thermal conductivity properties that promote the conduction of thermal energy from thermal energy source 106 to sensing region 102. Thermal conducting layer 204 can be formed from materials such as silicon nitride or silicon carbide. Deposition of silicon nitride or silicon carbide can be carried out using known techniques, such as chemical vapor deposition. The deposited thermal conducting layer 204 is patterned to form vias (not shown in FIG. 4D) over the formed aluminum contacts and interconnect lines to provide electrical contact thereto. As shown in FIG. 4E, after the silicon nitride layer 204 has been patterned, a metal layer 406, such as platinum, is deposited over thermal conducting layer 204 using a known technique such as chemical vapor deposition. This deposited layer of platinum 406 is then patterned to form temperature sensor 108, counter electrode 206, working electrode 208, and reference electrode 210. While the temperature sensor 108, counter electrode 206, working electrode 208 and reference electrode 210 can be made from the same metal, it should be understood that this is not required. Temperature sensor 108, counter electrode 206, working electrode 208, and reference electrode 210 can be formed from different materials.

Figure 4F:
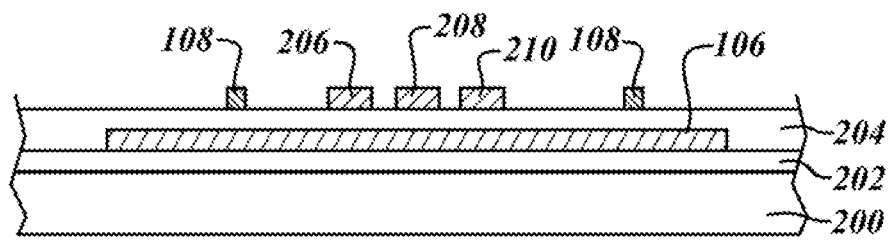

As illustrated in FIG. 4F, after the platinum layer 406 is patterned, a passivation layer 212 of polyimide is formed thereover. Polyimide can be applied by spin coating to form a uniform layer. The deposited polyimide layer is then patterned using known techniques to uncover electrodes 206, 208 and 210 and define sensing region 102. Portions of polyimide layer 212 that are not removed during the patterning step remain over and cover temperature sensor 108. After the polyimide is patterned, it is cured by heating followed by an oxygen plasma clean to remove organic contaminates.

Figure 4G:
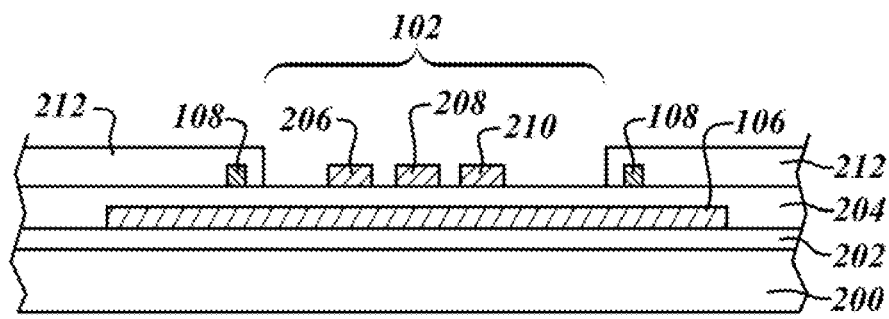

While passivation layer 212 in FIG. 4G is illustrated as covering temperature sensor 108, in other embodiments, passivation layer 212 can be patterned so that sensing region 102 is wider and includes temperature sensor 108. In other words, in other embodiments, temperature sensor 108 can be exposed in the same way that electrodes 206, 208 and 210 are not covered by passivation layer 212 and remain exposed. A sensor in accordance with this embodiment is schematically illustrated in FIG. 1.

Figure 5:
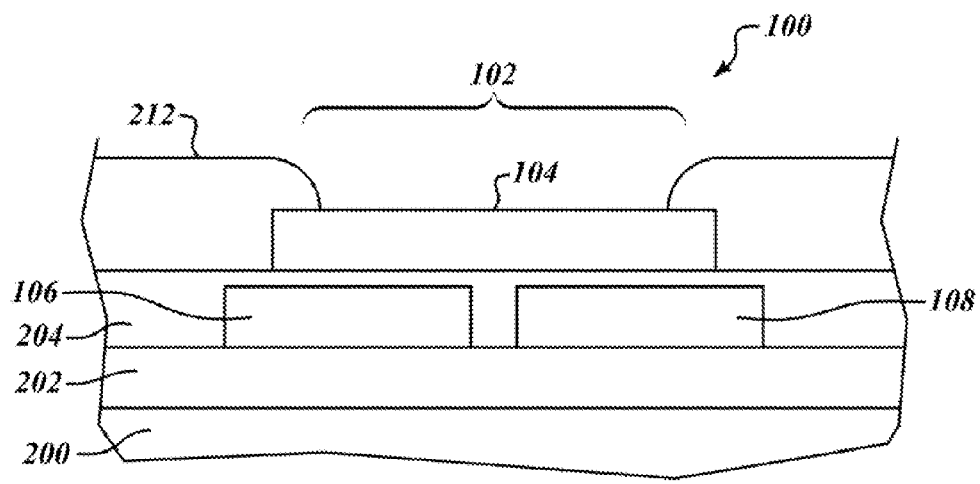
FIG. 5 shows a schematic of an alternative embodiment of a microsensor according to the present disclosure.

FIG. 5 shows an alternative embodiment of a microsensor 100 wherein thermal energy source 106 and temperature sensor 108 are adjacent to sensing region 102 that includes transducer 104. In the embodiment illustrated in FIG. 5, thermal energy source 106 and temperature sensor 108 are provided below sensing region 102. The description of thermal energy source 106 and temperature sensor 108 provided above with reference to FIGS. 1-4 is also applicable to FIG. 5. In the embodiment of FIG. 5, thermal energy source 106 and temperature sensor 108 are formed on thermal insulating layer 202. Thermal energy source 106 and temperature sensor 108 are separated from electrodes 104 by a thermal conducting layer 204. The transducer 104 forming part of sensing region 102 can include electrodes similar to those described above with reference to FIGS. 1-4. A portion of transducer 104 is exposed through passivation layer 212. The portions of passivation layer 212 that remain define the boundaries of sensor region 102. The semiconductor substrate 200 and thermal insulating layer 202 in FIG. 5 are described with reference to FIGS. 1-4 using the same reference numerals.

Figure 6:
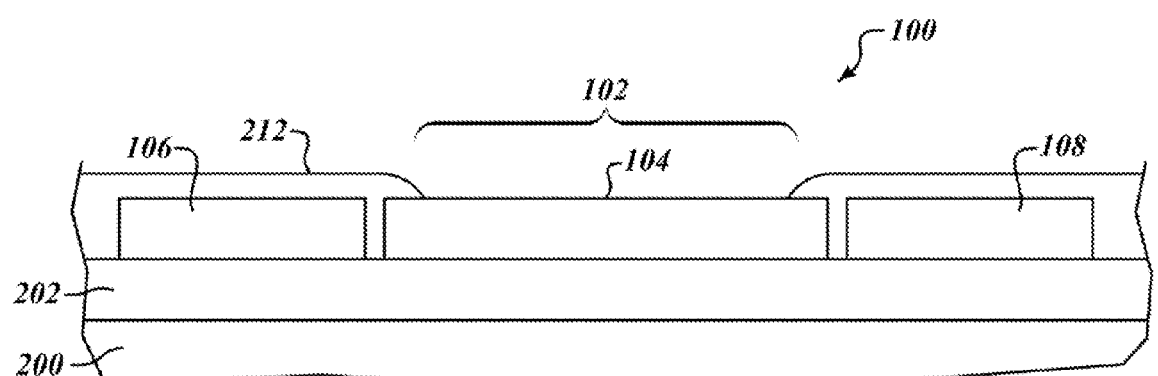
FIG. 6 shows a schematic view of another alternative embodiment of a microsensor of the present disclosure.

FIG. 6 shows another embodiment of sensor 100 wherein thermal energy source 106 and temperature sensor 108 are provided adjacent to, but not below, electrode component 104. In the embodiment illustrated in FIG. 6, thermal energy source 106, transducer 104 and temperature sensor 108 are each formed on thermal insulating layer 202. Passivation layer 212 covers thermal energy source 106 and temperature sensor 108 as well as a portion of transducer 104. The portion of transducer 104 that is exposed through passivation layer 212 defines sensor region 102. Other elements common between FIG. 6 and FIGS. 1-4 are identified by the same reference numerals.

Figure 7:
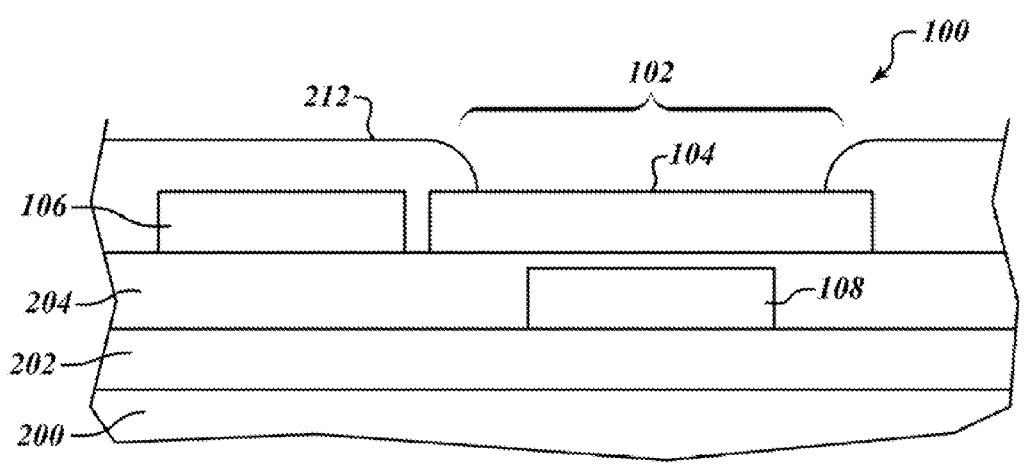
FIG. 7 shows a schematic view of another alternative embodiment of a microsensor of the present disclosure.

FIG. 7 shows another embodiment of sensor 100 wherein temperature sensor 108 is under transducer 104 and thermal energy source 106. In the embodiment illustrated in FIG. 7, temperature sensor 108 is formed over thermal insulating layer 202. Over temperature sensor 108 is formed a thermal conducting layer 204. Thermal energy source 106 and transducer 104 are formed over thermal conducting layer 204. A portion of transducer 104 and the thermal energy source 106 are covered by passivation layer 212. The portion of transducer 104 that is not covered by passivation layer 212 remains exposed and defines sensing region 102. Other elements common between FIG. 7 and FIGS. 1-4 are identified by the same reference numerals.

Each of the embodiments described by the present disclosure provide localized heating of sensor region 102. A semiconductor device may include multiple sensor regions 102 and localized heating can be provided to each sensing region and the temperature of each individual sensor region can be sensed and controlled utilizing the subject matter described in the present disclosure. By controlling the temperature of a sensing region through localized heating, variation in measurements resulting from taking multiple measurements at different temperatures can be reduced. In addition, by controlling the temperature of the sensing region, the rate of the interaction occurring in the sensing region, e.g., chemical reaction, can be made to approach the maximum rate which will increase the sensitivity of the microsensor. Increasing the sensitivity of the microsensor is particularly advantageous when the small dimensions of the sensor and/or the small volume of the samples result in small signals.

Localized heating produces a substantial difference in the temperature of the sensing region compared to the temperature of the region immediately surrounding the sensing region. For example, in accordance with certain embodiments described herein, the temperature of the sensing region can be increased by 20%, 60%, 100% or any other value compared to the temperature immediately surrounding the sensing region. In some instances, this increase in temperature of the sensing region can translate into the temperature of the sensing region being 10° C., over 20° C., or even greater than the temperature of the region immediately surrounding the sensing region. A temperature of the sensing region is selected which provides improved results at the transducer 104.

Figure 8:
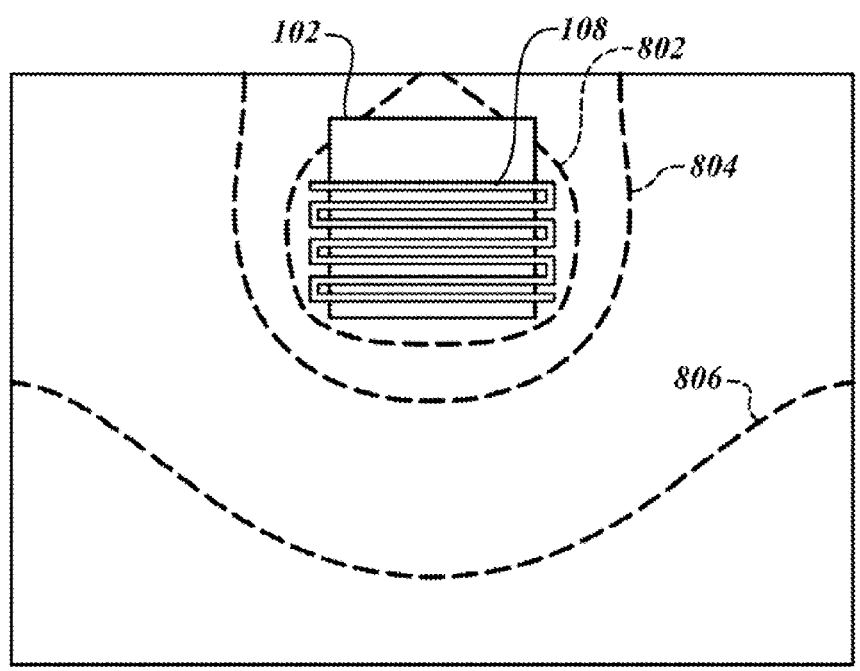
FIG. 8 shows a temperature profile model for a portion of a semiconductor die including a sensing region and thermal energy source in accordance with the embodiment of FIG. 2.

FIG. 8 shows a temperature contour image produced using thermal simulation software commercially available from Ansys, Inc. The simulation was based on the thermal energy source illustrated and described with reference FIG. 2 above. In the simulation, the following parameters were used:

Substrate was a 525 micrometer silicon die with 1 micrometer silicon dioxide layer;

Thermal energy source 108 was a serpentine tantalum aluminum line 10 micrometers wide and 0.02 micrometer thick having a sheet resistance of the 100 Ohms/square;

Thermal conducting layer was a 0.2 micrometer thick silicon nitride;

Passivation layer was polyimide;

Sensing region 102 formed by the opening in the polyimide layer accounted for 8% of the total die area;

No chemical solution was present in the exposed area;

5 milliamps of current was driven through the tantalum aluminum line.

Using these parameters, the simulation predicted an average temperature within the sensing region 102 formed by the opening in the polyimide of 47.5° C. Immediately outside the opening between sensing region 102 and contour line 802, the predicted temperature dropped to 28.845° C. The simulated temperature between contour lines 804 and 806 was 26.941° C. and the simulated temperature to the exterior of contour line 806 was 26.216° C. This simulation illustrates how the embodiments described herein provide localized heating to a sensor region of a microsensor.

In yet another embodiment, electrodes 206, 208 and 210 serve as a thermal energy source, a temperature sensor and also as port of the transducer. For example, counter electrode 206 can be cycled through various modes during which in a first mode it participates in the detection of the analyte and in a second mode it serves as a thermal energy source. In this embodiment, counter electrode 206 is formed from a material that allows it to participate in the sensing of the analyte in the sensing region and produce thermal energy when an electric current flows through it. In a similar manner, one of the electrodes 206, 208 and 210 can serve as an electrode that participates in the detection of the analyte and also serves as a temperature sensor. In this embodiment, such electrode, such as reference electrode 210 can be coupled to a control unit that cycles the reference electrode 210 through a sensing mode during which it participates in sensing of the analyte and a temperature sensing mode in which it detects the temperature of the sensing region 102.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A semiconductor device for detecting an analyte in a sample, the semiconductor device including a sensor comprising:

a sensing region formed over a semiconductor substrate, the sensing region including an electrochemical transducer that includes a working electrode and a counter electrode and is configured to detect an interaction between the analyte, the working electrode and the counter electrode when the sample is in the sensing region;

an integrated thermal energy source underlying the sensing region, the thermal energy source configured to produce thermal energy; and an integrated temperature sensor within the sensing region, the integrated temperature sensor configured to contact the sample and sense temperature of the sample when the sample is in the sensing region, the integrated temperature sensor being above the thermal energy source.

2. The semiconductor device of claim 1, further comprising a thermal conducting layer between the thermal energy source and the sensing region.

3. The semiconductor device of claim 1 wherein the temperature sensor and the electrochemical transducer are different devices.

4. The semiconductor device of claim 1, wherein one of the working electrode or counter electrode of the electrochemical transducer serves as the integrated temperature sensor.

5. A system for detecting an analyte in a sample, the system comprising:

a semiconductor device component including a sensor for detecting the analyte in the sample, the sensor including:

a sensing region formed over a semiconductor substrate, the sensing region including an electrochemical transducer that includes a working electrode and a counter electrode and is configured to detect an interaction between the analyte, the working electrode and the counter electrode when the sample is in the sensing region;

an integrated thermal energy source underlying the sensing region, the thermal energy source configured to produce thermal energy; and an integrated temperature sensor within the sensing region, the integrated temperature sensor configured to contact the sample and sense temperature of the sample when the sample is in the sensing region, the integrated temperature sensor being above the thermal energy source; and a control component configured to receive a signal from the integrated temperature sensor and provide a signal to the thermal energy source in response to the signal received from the integrated temperature sensor.

6. The system of claim 5, wherein the temperature sensor and the electrochemical transducer are different devices.

7. The system of claim 5, wherein one of the working electrode or counter electrode of the electrochemical transducer serves as the integrated temperature sensor.

8. A semiconductor device for detecting an analyte in a sample, the semiconductor device including a sensor comprising:

a sensing region formed over a semiconductor substrate, the sensing region including an electrochemical transducer that includes a working electrode and a counter electrode and is configured to detect an interaction between the analyte, the working electrode and the counter electrode when the sample is in the sensing region;

an integrated thermal energy source below the sensing region, the integrated thermal energy source configured to produce thermal energy and provide localized heating to the sensing region; and an integrated temperature sensor within the sensing region, the integrated temperature sensor configured to contact the sample and sense temperature of the sample when the sample is in the sensing region, the integrated temperature sensor being above the thermal energy source.

9. The semiconductor device of claim 8, wherein the temperature sensor and the electrochemical transducer are different devices.

10. The semiconductor device of claim 8, wherein one of the working electrode or counter electrode of the electrochemical transducer serves as the integrated temperature sensor.

11. A semiconductor device for detecting an analyte in a sample, the semiconductor device including a sensor comprising:

a sensing region formed over a semiconductor substrate, the sensing region including an electrochemical transducer that includes a working electrode and a counter electrode and is configured to detect an interaction between the analyte, working electrode and the counter electrode when the sample is in the sensing region;

an integrated thermal energy source below the sensing region, the integrated thermal energy source configured to produce thermal energy and provide localized heating to the sensing region; and an integrated temperature sensor within the sensing region, the integrated temperature sensor configured to contact the sample and sense temperature of the sample when the sample is in the sensing region, the thermal energy source being below the temperature sensor.

12. The semiconductor device of claim 11, wherein the working electrode, counter electrode, and temperature sensor are formed of the same metal.

13. A semiconductor device for detecting an analyte in a sample, the semiconductor device including a sensor comprising:

a sensing region formed over a semiconductor substrate, the sensing region including an electrochemical transducer that includes a working electrode and a counter electrode and is configured to detect an interaction between the analyte, the working electrode and the counter electrode when the sample is in the sensing region;

an integrated thermal energy source adjacent the sensing region, the integrated thermal energy source configured to produce thermal energy and provide localized heating to the sensing region; and an integrated temperature sensor within the sensing region, the integrated temperature sensor configured to contact the sample and sense temperature of the sample when the sample is in the sensing region, wherein the electrochemical transducer is between the integrated thermal energy source and the integrated temperature sensor.

14. The semiconductor device of claim 13, wherein the working electrode, counter electrode, and temperature sensor are formed of the same metal.

15. The semiconductor device of claim 13, wherein the temperature sensor and the electrochemical transducer are different devices.

16. The semiconductor device of claim 13, wherein one of the working electrode or counter electrode of the electrochemical transducer serves as the integrated temperature sensor.

17. A semiconductor device for detecting an analyte in a sample, the semiconductor device including a sensor comprising:

a sensing region formed over a semiconductor substrate, the sensing region including an electrochemical transducer that includes a working electrode and a counter electrode and is configured to detect an interaction between the analyte, the working electrode and the counter electrode;

an integrated thermal energy source underlying the sensing region, the thermal energy source configured to produce thermal energy; and one of the working electrode or the counter electrode serving as an integrated temperature sensor adjacent the sensing region, the integrated temperature sensor configured to sense temperature of the sensing region and the integrated temperature sensor being above the thermal energy source.

\* \* \* \* \*